United States Patent [19]

Usui et al.

[11] Patent Number: 5,208,151
[45] Date of Patent: May 4, 1993

[54] PROCESS FOR THE PREPARATION OF DERIVATIVES OF MALTOOLIGOSACCHARIDES

[75] Inventors: Taichi Usui, Shizuoka; Teruo Nakakuki, Mishima; Kazuo Sakai, Yaizu, all of Japan

[73] Assignees: Nihon Shokuhin Kako Co., Ltd., Tokyo; Yaizu Suisan Kagaku Kogyo Co., Ltd., Yaizu, both of Japan

[21] Appl. No.: 607,612

[22] Filed: Oct. 31, 1990

Related U.S. Application Data

[63] Continuation of Ser. No. 568,525, Aug. 14, 1990, abandoned, which is a continuation of Ser. No. 434,516, Nov. 14, 1989, abandoned, which is a continuation of Ser. No. 234,019, Aug. 18, 1988, abandoned.

[51] Int. Cl.$^5$ .................. C12P 19/20; C12P 19/14; C07G 3/00; C07H 15/00
[52] U.S. Cl. .................. 435/99; 435/96; 435/101; 435/200; 435/201; 435/202; 536/18.5; 536/100; 536/124
[58] Field of Search .................. 435/99

[56] References Cited

U.S. PATENT DOCUMENTS

| | | | |
|---|---|---|---|
| 4,219,571 | 8/1980 | Miyake | 435/99 |
| 4,225,672 | 9/1980 | Hall | 435/193 |
| 4,595,418 | 6/1986 | Yoshino | 435/99 |
| 4,621,137 | 11/1986 | Miyake et al. | 435/97 |

OTHER PUBLICATIONS

Usui and Murata, *The Japanese Biochemical Society*, vol. 59, No. 8, Aug. 25, 1987, p. 898 (abstract).
Usui, Murata and Takayama, *The Agricultural Chemical Society of Japan*, vol. 62, No. 3, Mar. 15, 1988, p. 337 (abstract).
Usui and Murata, XIth Japanese Carbohydrate Symposium, Jul. 25 and 26, 1988, p. 103 (abstract).
J. Jap. Soc. Starch Sci., vol. 29, No. 1, pp. 27–33 (1982) T. Nakakuki et al., "Fractionation of Maltosaccharides by Gel Filtration".
Journal of Chromotography, 150, (1978) 242–245; Umeki et al., "Fractionation of Maltosaccharides of Relatively High Degree of Polymerization by Multiple Descending Paper Chromatography".
Journal of Chromatography, 121, 361–369 (1976); Kainuma et al., "Gel Permeation Chromatography of Maltosaccharides on Polyacrylamide Gel".
Carbohydrate Research, 128 (1984) 297–310; Nakakuki et al., "Action Patterns of Various Exo-Amylases and the Anomeric Configurations of their Products".
Process Biochemistry, (Jun. 1987) 78–81; Saha et al., "Biotechnology of Maltose Syrup Production".

*Primary Examiner*—Johnnie R. Brown
*Assistant Examiner*—Pamela S. Webber
*Attorney, Agent, or Firm*—Frishauf, Holtz, Goodman & Woodward

[57] ABSTRACT

Highly purified derivatives of maltooligosaccharides can be produced at a high yield by reacting, in a mixture of a hydrophilic organic solvent and water, a mixture of maltooligosaccharides or a substance capable of being converted into the maltooligosaccharides upon reaction with an amylase, and an o-glucosyl derivative, with the amylase.

The resulting derivatives of maltooligosaccharides are useful as a substrate for the determination of $\alpha$-amylase activity in a humor, physiologically active substances, natural dieteic sweetenings, coloring agents and the like.

14 Claims, No Drawings

PROCESS FOR THE PREPARATION OF DERIVATIVES OF MALTOOLIGOSACCHARIDES

This application is a continuation of application Ser. No. 07/568,525, filed Aug. 14, 1990, now abandoned; which is a continuation of Ser. No. 07/434,516 filed Nov. 14, 1989 (abandoned); which is a Ser. No. 07/234,019 filed Aug. 18, 1988 (abandoned).

BACKGROUND OF THE INVENTION

1. Field of the Invention

The present invention relates to a novel process for the preparation of derivatives of maltooligosaccharides. More particularly, the present invention relates to a process for the preparation of derivatives of maltooligosaccharides having a high purity at a high yield.

The derivatives of maltooligosaccharides have been widely used as a substrate for determining α-amylase activity in human serum and urine, various physiologically active substances, natural dieteic sweetenings, coloring agents and the like. For example, when the derivatives of maltooligosaccharides are used as a substrate for the determination of α-amylase activity of the humor, there are advantages that such determination can be easily and simply carried out, and that said derivatives have a good adaptability to the analysis made using automatic analytical instruments.

2. Description of Related Art

Hitherto, a chemical synthetic process and an enzyme process have been known and used in the production of derivatives of maltooligosaccharides such as α,β-phenylmaltooligosaccharides and the like.

A chemical synthetic process can be carried out as follows (see, Japanese Unexamined Patent Publication (Kokai) No. 54-25893): First, maltooligosaccharides such as maltopentaose or maltohexaose are acetylated to protect hydroxyl groups thereof. The acetylated maltooligosaccharides are then halogenated to introduce halogens into the reducing-end of maltooligosaccharides. Thereafter, the resultant halogenated acetylated maltooligosaccharides are reacted with substituted phenols in the presence of solvents such as pyridine and the like to obtain acetylated product of α,β-substituted phenylmaltooligosides. The acetylated product is subjected to deacetylation to obtain a desired α or β-substituted phenylmaltooligoside.

An enzyme process can be made as follows (see, *Carbohydrate Research* 61 (1978), 359-368): Alpha(α)-cyclodextrin and α,β-phenylglucosides are reacted with transferases such as cyclodextrin glucosyltransferase or the like to produce a mixture of α,β-phenylmaltooligosides. The resulting mixture is the fractionated by means of a column chromatography to obtain a desired α or β-phenylmaltooligoside, for example, 4-nitrophenyl-α-D-maltoheptaoside.

Among these processes, the chemical synthetic process has, however, drawbacks such that the steps necessary to complete the process are numerous and troublesome, that the yield is low, and that α- or β-linked derivatives can not be freely produced.

Also, while the enzyme process can be easily carried out due to simpleness of the reaction steps thereof, it has a tendency to produce a large amount of homologues which have a molecular weight close to that of the desired product. Thus, an actual product comprises a mixture of various oligosides having different degrees of polymerization of glucose. Therefore, to obtain a highly purified product, it was necessary to further carry out fractionation by using a chromatography. Moreover, this enzyme process had a drawback that a yield of the product is low.

In addition, as described in the above paragraph, derivatives of maltooligosaccharides having a high purity are required, when such derivatives are used as a substrate for the determination of activity of α-amylase in a humor. However, the above-described prior art processes are not satisfactory for this requirement, because using these processes, it is very difficult to produce highly purified derivatives of maltooligosaccharides.

SUMMARY OF THE INVENTION

An object of the present invention is to provide a process for the preparation of derivatives of maltooligosaccharides which enables the production of derivatives of maltooligosaccharides having a high purity at a high yield.

According to the present invention, there is provided a process for the preparation of derivatives of maltooligosaccharides, characterized in that amylase is acted on a mixture of the maltooligosaccharides or a substance capable of being converted into the maltooligosaccharides upon reaction with the amylase, and an o-glucosyl derivative, in a mixture of a hydrophilic organic solvent and water.

When amylase is acted on a mixture of the maltooligosaccharides or a substance which is converted into the ma tooligosaccharides through the reaction with the amylase (both of them are referred hereinafter to as "maltooligosaccharides and the like"), and an o-glucosyl derivative, two reactions are caused. One reaction is a hydrolysis reaction in which the maltooligosaccharides and the like are hydrolyzed to produce maltooligosaccharides having a lower molecular weight. Another reaction is a transfer reaction in which the o-glucosyl derivative acts as an acceptor and the maltooligosaccharides act as a donor.

When the above reaction process is carried out in an aqueous solution, the hydrolysis reaction can rapidly proceed thereby producing maltooligosaccharides having a lower molecular weight as a principal product. However, when said process is carried out in a mixture of a hydrophilic organic solvent and water, surprisingly and unexpectedly, said transfer reaction can be remarkably accelerated and therefore the desired derivatives of maltooligosaccharides can be produced at a higher yield.

The produced derivatives of maltooligosaccharides can be fractionated by using a fractionation technique such as column chromatography, extraction with solvent or the like, to obtain those having a higher purity.

Therefore, according to the present invention, highly purified derivatives of maltooligosaccharides can be produced at a higher yield by using a relatively simple method in which amylase is acted on a mixture of maltooligosaccharides and the like and o-glucosyl derivative.

DESCRIPTION OF THE PREFERRED EMBODIMENTS

The "maltooligosaccharides" used in the present invention are maltooligosaccharides wherein the degree of polymerization of glucose is principally 2 to 7. Examples of these maltooligosaccharides include maltose, maltotriose, maltotetraose, maltopentaose, maltohexaose, maltoheptaose and the like. These maltooligosaccharides may be used alone or in combination. Further, as an alternative maltooligosaccharide a decomposition product of starch which contains maltooligosaccharides as a main component may be also used. Furthermore, in addition to the maltooligosaccharides, any substance capable of being converted into the maltooligosaccharides upon reaction with the amylase simultaneously used ma be also used in the present invention. The substance capable of being converted into the maltooligosaccharides is, for example, a decomposition product of starch which can be reacted with the amylase to principally produce maltooligosaccharides with a polymerization degree of 2 to 7.

The o-glucosyl derivative used in combination with said maltooligosaccharides and the like in the present invention is an o-glucosyl compound which contains glucose at the non-reducing end of the saccharide portion thereof.

For example, the o-glucosyl derivative used in the preparation of α or β-phenylmaltooligoside which is useful as a substrate for the α-amylase activity determination includes 4-nitrophenyl-α-D-glucoside, 4-nitrophenyl-β-D-glucoside, 2-chloro-4-nitrophenyl-α-D-glucoside, 2-chloro-4-nitrophenyl-β-D-glucoside, 2,4-dichlorophenyl-β-D-glucoside, 2,6-dichloro-4-nitrophenyl-β-D-glucoside and the like.

Further, examples of the o-glucosyl derivative with a physiological activity are arbutins useful as a diuretic, coniferins useful as an antitussive, phenol glycosides such as s licin and the like which are useful as an analgesic, coumarin glycosides such as aesculin and the like which are useful as a dermatotherapic medicament or an ophthalmitic medicament, anthracene glycosides such as sennosides A and B and the like which are useful as an abstergent, steviosides useful as a stomachic, antasthenic and sweetening, terpene glycosides such as verbenaline and the like which are useful as a coagulant and uterotonic, bitter glycosides such as gentiopicrin and the like which are useful as an antimalarial medicament, steroid glycosides such as gigitonin and the like which are useful as a cholesterol precipitant, cardiac glycosides such as scillaren A, lanataglycoside C and the like which have a cardiotonic effect, gibberellin glycosides such as different types of gibberellin glycosides having a plant growth effect, lignan glycosides such as pinoresinol diglucoside and the like which have hypotensive and entatic effects, and similar compounds.

However, the o-glucosyl derivative used in the present invention should not be restricted to those listed above. Any compound may be used as the o-glucosyl derivative in the present invention, insofar as it contains glucose at the non-reducing end of the saccharide moiety thereof. Further, α- and β-forms of the o-glucosyl derivative may be equivalently used in the present invention. Use of said α-forms will result in α-maltooligoside, while use of said β-forms will result in β-maltooligoside.

Amylase is also used as a reaction component in the present invention. Any amylase may be used herein, insofar as it is an enzyme which can hydrolyze starch. However, to attain an effective production of the desired derivatives of maltooligosaccharides, it is preferred to use a maltooligosaccharide-producing amylase or glucoamylase as the amylase. For example, glucoamylase, maltotriose-producing amylase, maltose-producing amylase, maltopentaose-producing amylase, maltohexaose-producing amylase and the like are more preferably used as the amylase.

The maltose-producing amylase includes β-amylase originated from plants such as soybean, malt and the like, and in addition to these, maltose-producing amylases originated from microorganisms. Suitable microorganisms are, for example Bacillus polymyxa (J. Robyt and D. French, Arch. Biochem. Biophys., 104, 338 (1964)), Bacillus cereus, Y. Takasaki, Agric. Biol. Chem., 40, 1515–1523 (1976)), Pseudomonas sp. (S. Shinke et al., J. Ferment. Technol. 53, 693–698 (1975)), Streptomyces hygroscopicus (Y. Hidaka et al., Stärke, 26, 413 (1974)), Streptomyces praecox (K. Wakao et al., Denpun Kagaku (Journal of the Japanese Society of Science), 25, 155 (1978)) and the like.

Other known amylases which can produce oligosaccharides having a polymerization degree of glucose, equivalent to or higher than that of maltotriose include:

Maltotriose-producing amylase, for example, that originated from Streptomyces griseus (Wakao et al., Denpun Kagaku (Journal of the Japanese Society of Science), 26, 175 (1979)) and that originated from Bacillus sp. [Y. Takasaki, 1983 Annual Meeting of Nihon Nogeikagaku Gakkai (the Agricultural Chemical Society of Japan), P.169 (1983)].

Maltotetraose-producing amylase, for example, that originated from Pseudomonas stutzeri (J. F. Robyt and R. J. Ackerman, Arch. Biochem. Biophys., 145, 105 (1971)).

Maltopentaose-producing amylase, for example, that originated from Bacillus licheniformis (N. Saito, Arch. Biochem. Biophys., 155, 290 (1973)) and those described in Kobayashis et al., 1983 Annual Meeting of Nihon Denpun Gakkai (the Starch Society of Japan), P.301 (1983), and Yoshigi et al., 1984 Annual Meeting of Nihon Nogei-Kagaku Gakkai (the Agricultural Chemical Society of Japan), P.584 (1984).

And, maltohexaose-producing amylase, for example, that originated from Aerobacter aerogenes (K. Kainuma et al., FEBS Lett., 26, 281 (1972), and those described in J. F. Kennedy and C. A. White, Stärke, 31, 93 (1979), Taniguchi et al., Denpun Kagaku (Journal of the Japanese Society of Science), 29, 107 (1982) and Y. Takasaki, Agric. Biol. Chem., 47, 2193 (1983).

In the preparation process according to the present invention, the above-described maltooligosaccharides and the like and o-glucosyl derivative as a mixture are reacted with the above amylase in a mixture of a hydrophilic organic solvent and water.

The hydrophilic organic solvent used herein is not limited, but it is particularly preferred to use a water-miscible organic solvent. Examples of suitable hydrophilic organic solvent include methanol, ethanol, n-propanol, isopropanol, acetone, dioxane, formamide, dimethylformamide, dimethylsulfoxide, ethylene glycol, propylene glycol and the like. Among these solvents, alcoholic solvents are particularly suitable.

The hydrophilic organic solvents described above may be used alone, or two or more of them may be mixed for use, if desired.

A content of the hydrophilic organic solvent in the mixed solvent with water depends on various factors such as types of the solvents used and types of the substrates. The content of the organic solvent used is suitably about 20 to 80% by volume, more preferably about 30 to 70% by volume, based on the volume of the mixed solvent.

The reaction conditions of the present process will be described hereinafter.

In the reaction of the present invention, a molar ratio of the maltooligosaccharides and the like to the o-glucosyl derivative is not specially restricted. Such molar ratio can be suitably determined in view of a solubility of said saccharides and the like and o-glucosyl derivative in a reaction solvent used, a reaction velocity, an yield, an economics and other factors. Generally, a molar ratio of the maltooligosaccharides or a substance capable of being converted into the maltooligosaccharides upon reaction with the amylase to the o-glucosyl derivative is preferably in the range of from about 1:1 to about 1:5.

Also, a combined concentration of the maltooligosaccharides or a substance capable of being converted into the maltooligosaccharides upon reaction with the amylase and the o-glucosyl derivative in the mixed solvent can be determined in view of a solubility of said maltooligosaccharides and the like and o-glucosyl derivative in said solvent, a reaction velocity, an yield and the like, as in the molar ratio described above. Generally, the combined concentration of 10 to 60% by weight, more preferably 20 to 50% by weight is suitable.

The reaction can be generally carried out nearly at a temperature suitable for the amylase. The reaction temperature is preferably is in the range of about 20° to 60° C. It can be selected depending upon a type of the enzyme used, a reaction velocity, or the like. During reaction, a pH value is selected so that it becomes equal to or close to a pH value suitable for the enzyme used. Suitable pH value is generally in the range of about 4 to 8.

The reaction time varies depending upon various factors such as a reaction temperature and an amount of the enzyme used, but suitable reaction time is generally about 2 to 120 hours, more preferably about 12 to 48 hours.

The reaction can be carried out batch-wise or in a continuous process. A soluble enzyme is used in the batch process, while an immobilized enzyme is used in the continuous process. After completion of the reaction, to terminate an enzyme reaction, a reaction mixture is acidified or alkalized, or heated. The mixture is then subjected to a column chromatography, solvent extraction or the like to conduct fractionation. As a result of this fractionation, a desired derivative of maltooligosaccharides can be obtained.

Further, when fractionation is carried out, a fraction of unreacted o-glucosyl derivative can be recovered to repeatedly use said derivative in the subsequent processes. Recovery of the unreacted o-glucosyl derivative is effective to increase the yield of the derivatives of maltooligosaccharides with regard to the starting o-glucosyl derivative.

A principal reaction of the present process is represented by the following reaction formula:

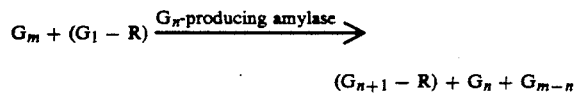

$$(G_{n+1} - R) + G_n + G_{m-n}$$

in which $G_m$ and $G_n$ each represented a maltooligosaccharide having a polymerization degree of glucose of m and n, respectively, and $(G_1$-$R)$ represents an o-glucosyl derivative wherein R means an aglycone moiety. A polymerization degree of saccharide in the saccharide moiety of the o-glucosyl derivative may be 1 or more, but herein $G_1$ refers to only glucose positioned at the non-reducing end of said derivative. Said symbols "m" and "n" which represent a polymerization degree of glucose are integers and satisfy the relationships: $n < m < 2n$ and $n = 1$ to 6.

When the above reaction is carried out in an aqueous solution, a rapid hydrolysis reaction is caused, thereby resulting in $G_n$ and $G_{m-n}$ as main products. Only lesser amounts of $(G_{n+1}-R)$, maltooligoside derivative, is produced, because the transfer reaction concurrently occurred is insignificant. It is therefore very difficult to prepare and collect the derivatives of maltooligosaccharides by using said reaction in an aqueous solution.

In contrast, when said reaction is performed in a mixture of a hydrophilic organic solvent and water according to the present invention, a hydrolysis reaction is inhibited, but a transfer reaction in which the o-glucosyl derivative acts as an acceptor and the maltooligosaccharides and the like act as a donor is remarkably accelerated.

In other words, according to the present invention, it becomes possible to effectively produce derivatives of maltooligosaccharides by using a very simple and easy process that the maltooligosaccharides and the like and the o-glucosyl derivative are reacted with the amylase in a mixture of the hydrophilic organic solvent and water.

Using the preparation process of the present invention, there is provided a derivative of maltooligosaccharides comprising maltooligosaccharides having bonded thereto a chromophore as an aglycone. This derivative of maltooligosaccharides is useful as a substrate for the determination of α-amylase activity in a humor. Namely, since this derivative of maltooligosaccharides can liberate a chromophore therefrom if reacted with α-amylase in the presence of α-glucosidase and/or β-glucosidase, it can be usefully utilized as a substrate for the determination of an activity of α-amylase which is contained in the humor, for example, human serum, urine and the like.

Using the preparation process of the present invention, there is also provided a glycoside of maltooligosaccharides having the maltooligosaccharides bonded to a glucose residue of the o-glucosyl glycosides which possess a physiologic activity, for example. This type of the glycoside in which the maltooligosaccharides are being bonded to a saccharide portion thereof will show improved properties such as solubility, taste, physiological activity, stability and the like.

Next, the present invention will be further described with reference to some examples thereof. Note, the present invention should not be limited to the following examples.

EXAMPLE 1

Preparation of 4-nitrophenyl-β-D-maltopentaoside 240 mg (0.29 mM) of maltopentaose and 260 mg (0.86 m mole) of 4-nitrophenyl-β-D-glucoside (molar ratio of 1:3) are added to a 1:1 solution of 15 m mol acetate buffer (pH 6.0) and methanol to make a total amount of 1 ml.

To the mixture, added is 0.2 units of maltotetraose-producing amylase which was originated from Pseudomonas stutzeri. Herein, one (1) unit means an amount of enzyme necessary to decompose 1 μmol of glucoside linkage per minute, when 1% soluble starch is used as a substrate. The reaction is continued at 30° C. for 48 hours.

After the reaction has been completed, 0.2M borate buffer (pH 9.8) is added to the reaction mixture to terminate the reaction. The mixture is then concentrated. The reaction product is fractionated with a gel permeation column chromatography using Bio-Gel-p2 to obtain 90 mg (yield 32.7%) of 4-nitrophenyl-$\beta$-D-maltopentaoside, purity 99.2%. Nuclear magnetic resonance (NMR) spectrum indicates that the product collected after the fractionation is exactly 4-nitrophenyl-$\beta$-D-maltopentaoside.

EXAMPLE 2

Preparation of 4-nitrophenyl-$\alpha$-D-maltopentaoside 120 mg (0.14 mM) of maltopentaose and 84 mg (0.28 mM) of 4-nitrophenyl-$\alpha$-D-glucoside (molar ratio of 1:2) are dissolved in a methanol-acetate buffer (pH 6.0) (50% of methanol) to make a total amount of 1 ml. To the solution, added is 0.2 units of maltotetraose-producing amylase. The reaction is continued at 30° C. for 20 hours.

After the reaction has been completed, the reaction mixture is treated in the procedure similar to that of said Example 1. 18 mg (yield 13.1%) of 4-nitrophenyl-$\alpha$-D-maltopentaoside, purity 99.5%, is thus obtained.

The NMR spectrum indicates that the product collected after the fractionation is exactly 4-nitrophenyl-$\alpha$-D-maltopentaoside.

EXAMPLE 1

Preparation of 4-nitro-2-chlorophenyl-$\beta$-D-maltoheptaoside 600 mg (0.52 mM) of maltoheptaose and 700 mg (2.08 m mol) of 4-nitro-2-chlorophenyl-$\beta$-D-glucoside (molar ratio of 1:4) are added to a solution of methanolacetate buffer (15 m mol, pH 6.0) (40% of methanol) to make a total amount of 5 ml.

To the mixture, added is 0.4 units ("unit" is defined in said Example 1) of maltoheptaose-producing amylase which was originated from *Aerobacter aerogenes*. The reaction is continued at 30° C. for 18 hours.

After the reaction has been completed, the reaction mixture is treated in the procedure similar to that of said Example 1. 120 mg (yield 15.2%) of 4-nitro-2-chlorophenyl-$\beta$-D-maltoheptaoside, purity 98.9%, is thus obtained.

The NMR spectrum indicates that the product collected after the fractionation is exactly 4-nitro-2-chlorophenyl-$\beta$-D-maltoheptaoside.

We claim:

1. A process for the preparation of a derivative of maltooligosaccharide comprising an $\alpha$-phenylmaltooligoside or a $\beta$-phenylmaltooligoside wherein the phenyl or substituted phenyl group thereof contains two or more glucoses bonded thereto or a derivative of maltooligosaccharide having two or more glucoses bonded to aglycone selected from the group consisting of phenol glycosides, coumarin glycosides, anthracene glycosides, terpene glycosides, bitter glycosides, steroid glycosides, cardiac glycosides, gibberellin glycosides and lignan glycosides comprising reacting amylase and a mixture of (i) at least one maltooligosaccharide or a decomposition product of starch capable of being converted into the maltooligosaccharides upon reaction with the amylase, and (ii) an o-glycosyl derivative, in a mixture of a hydrophilic organic solvent and water.

2. The process according to claim 1 in which said hydrophilic organic solvent is methanol, ethanol, n-propanol, isopropanol, acetone, dioxane, formamide, dimethylsulfoxide, ethylene glycol, propylene glycol or a mixture thereof.

3. The process according to claim 1 in which said at least one maltooligosaccharide is a maltooligosaccharide with a degree of polymerization of glucose of 2 to 7.

4. The process according to claim 1 in which said amylase is a maltooligosaccharide-producing amylase or glucoamylase.

5. The process according to claim 1 in which the content of hydrophilic organic solvent in said mixed solvent is 20 to 80% by volume.

6. The process according to claim 1 in which a molar ratio of said at least one maltooligosaccharide or said decomposition product to said o-glycosyl derivative is 1:1 to 1:5.

7. The process according to claim 1 in which a combined concentration of said at least one maltooligosaccharide or said decomposition product and said o-glucosyl derivative in said mixed solvent is 10 to 60% by weight.

8. The process according to claim 1 in which the reaction is carried out at a pH value of 4 to 8.

9. The process according to claim 1 in which the reaction time is 2 to 120 hours.

10. The process according to claim 2, wherein said maltooligosaccharides are maltooligosaccharides with a degree of polymerization of glucose of 2 to 7; said amylase is a maltooligosaccharide-producing amylase or glucoamylase; the hydrophilic organic solvent is contained in a mixture with water in an amount of 20 to 80 volume %; a molar ratio of said maltooligosaccharide or said decomposition product to said o-glycosyl derivative is 1:1 to 1:5; a combined concentration of said maltooligosaccharide or said decomposition product and said o-glucosyl derivative in said mixed solvent is 10 to 60% by weight; and the process is carried at a pH of 4 to 8 and for a time period of 2 to 120 hours.

11. The process according to claim 10, wherein the maltooligosaccharide is selected from the group consisting of maltose, maltotriose, maltotetraose, maltopentaose, maltohexaose, and maltoheptaose.

12. The process according to claim 10, wherein the o-glucosyl derivative is selected from the group consisting of 4-nitrophenyl-$\alpha$-D-glucoside, 4-nitrophenyl-$\beta$-D-glucoside, 2-chloro-4-nitrophenyl-$\alpha$-D-glucoside, 2-chloro-4-nitrophenyl-$\beta$-D-glucoside, 2,4-dichlorophenyl-$\beta$-D-glucoside, 2,6-dichloro-4-nitrophenyl-$\beta$-D-glucoside, arbutins, coniferins, salicin, aesculin, sennoside A, sennoside B, steviosides, verbenaline, gentiopicrin, gigitonin, scillaren A, lantaglycoside C, gibberellin glycosides and pinoresinol diglucoside.

13. The process according to claim 10, wherein the amylase is selected from the group consisting of glycoamylase, maltose-producing amylase, maltotriose-producing amylase, maltopentaose-producing amylase and maltohexaose-producing amylase.

14. The process according to claim 10, wherein the content of the organic solvent is 30 to 70 volume %, based on the volume of the mixed solvent; the combined concentration of said maltooligosaccharide or said decomposition product and said o-glucosyl derivative in said mixed solvent is 20 to 50% by weight; and the process is carried at a temperature of 20° to 60° C. for 12 to 48 hours.

* * * * *